(12) United States Patent
Sano et al.

(10) Patent No.: US 9,376,416 B2
(45) Date of Patent: Jun. 28, 2016

(54) COMPOSITION CONTAINING SCIRPUSIN B, AND PROCESS FOR PRODUCING COMPOSITION CONTAINING SCIRPUSIN B

(75) Inventors: Shoko Sano, Yokohama (JP); Kenkichi Sugiyama, Yokohama (JP)

(73) Assignee: MORINAGA & CO., LTD., Tokyo (JP)

(\*) Notice: Subject to any disclaimer, the term of this patent is extended or adjusted under 35 U.S.C. 154(b) by 467 days.

(21) Appl. No.: 14/111,476

(22) PCT Filed: Apr. 22, 2011

(86) PCT No.: PCT/JP2011/059926
§ 371 (c)(1),
(2), (4) Date: Oct. 11, 2013

(87) PCT Pub. No.: WO2012/144064
PCT Pub. Date: Oct. 26, 2012

(65) Prior Publication Data
US 2014/0039049 A1 Feb. 6, 2014

(30) Foreign Application Priority Data
Mar. 18, 2010 (JP) ................. 2010-063027

(51) Int. Cl.
| A23L 1/00 | (2006.01) |
| A23L 2/38 | (2006.01) |
| A01N 65/00 | (2009.01) |
| A61K 36/00 | (2006.01) |
| C07D 307/80 | (2006.01) |
| A23L 1/30 | (2006.01) |
| A61K 8/49 | (2006.01) |
| A61Q 19/00 | (2006.01) |
| A61K 8/97 | (2006.01) |

(52) U.S. Cl.
CPC ............ *C07D 307/80* (2013.01); *A23L 1/3002* (2013.01); *A61K 8/498* (2013.01); *A61K 8/97* (2013.01); *A61Q 19/00* (2013.01); *A61K 2800/10* (2013.01)

(58) Field of Classification Search
USPC .................. 549/462, 466, 469; 514/469, 470; 424/725, 776; 426/430, 598
See application file for complete search history.

(56) References Cited

U.S. PATENT DOCUMENTS

2012/0004322 A1\* 1/2012 Matsui .................. A23L 1/3002 514/772

FOREIGN PATENT DOCUMENTS

| JP | 04-159280 A | 6/1992 |
| JP | 2009-102298 A | 5/2009 |
| JP | 2009-102299 A | 5/2009 |
| JP | 2010-030911 A | 2/2010 |
| JP | WO 2010113315 A1 \* | 10/2010 ............ A23L 1/3002 |
| TW | 201036648 A1 | 10/2010 |
| WO | 2010/113315 A1 | 10/2010 |
| WO | WO 2010113315 A1 \* | 10/2010 |

OTHER PUBLICATIONS

Matsui, Y. et al., (Acta Horticulturae 841 (Proceedings of the IInd International Symposium on Human Health Effects of Fruits and Vegetables, pp. 557-561) Published 2009.\*
Sano, S. et al., (J. Agric. Food. Chem. vol. 59, pp. 6209-6213, published online Apr. 28, 2011).\*
Powell, R.G., et al (Journal of Natural Products, vol. 50, pp. 293-296, published 1987).\*
80% ethanol MSDS page. BBC Chemical. Published online Jan. 10, 2004.\*
Kobayashi, K. et al., Biol. Pharm. Bull. vol. 29, pp. 1275-1277. Published 2006.\*
Yutaka Matsumoto et al., "B1-2 Passionfruit Shushi ni Fukumareru Polyphenol Seibun no Kanjunkan Kaizen Sayo", Dai 17 Kai Japan Mibyou System Association Gakujutsu Sokai Shorokushu, 2010, p. 94.
Yuko Matsui, et al., "Extract of Passion Fruit (*Passiflora edulis*) Seed Containing High Amounts of Piceatannol Inhibits Melanogenesis and Promotes Collagen Synthesis", J Agric Food Chem., 2010, pp. 11112-11118, vol. 58, No. 20.
Kyoko Kobayashi, et al., "Constituents of Stem Bark of *Callistemon rigidus* Showing Inhibitory Effects on Mouse a-Amylase Activity", Biol. Pharm. Bull, 2006, pp. 1275-1277, vol. 29, No. 6.
Guo-Xun Yang, et al., "Anti-HIV Bioactive Stilbene Dimers of *Caragana rosea*", Planta Med, 2005, pp. 569-571, vol. 71.
Ting Xiang, et al., "Antioxidant Constituents of *Caragana tibetica*", Chem. Pharm. Bull., 2005, pp. 1204-1206, vol. 53, No. 9.
G. Schmeda-Hirschmann et al., "Biological Activity and Xanthine Oxidase Inhibitors from *Scirpus californicus* (C.A. Mey.) Steud.", Phytotherapy Research, 1996, pp. 683-685, vol. 10.
Extended European Search Report issued Sep. 15, 2014 in European Patent Application No. 11863866.7.
Chinese Office Action issued Jul. 7, 2014 in Chinese Patent Application No. 201180070206.6.

\* cited by examiner

*Primary Examiner* — Paul Zarek
*Assistant Examiner* — George W Kosturko
(74) *Attorney, Agent, or Firm* — Sughrue Mion, PLLC

(57) ABSTRACT

Provided are: a composition containing scirpusin B, which is a composition derived from a natural material and contains scirpusin B at a high content; and a process for producing the composition containing scirpusin B. A composition containing scirpusin B is produced by the extraction from a passion fruit seed. In the extraction of scirpusin B, the passion fruit seed is crushed, and subsequently at least one solvent selected from a hydrous alcohol solvent and a hydrous ketone solvent is added to the crushed product to thereby extract scirpusin B into the solvent.

5 Claims, 3 Drawing Sheets

COMPOSITION CONTAINING SCIRPUSIN B, AND PROCESS FOR PRODUCING COMPOSITION CONTAINING SCIRPUSIN B

CROSS REFERENCE TO RELATED APPLICATIONS

This application is a National Stage of International Application No. PCT/JP2011/059926 filed Apr. 22, 2011, the contents of all of which are incorporated herein by reference in their entirety.

TECHNICAL FIELD

The present invention relates to a scirpusin-B-containing composition containing scirpusin B derived from passion fruit seeds, and a method for manufacturing a scirpusin-B-containing composition.

BACKGROUND ART

Passion fruit is a plant in the genus *Passiflora*, family Passifloraceae, known otherwise as *kudamono tokeiso*. The fruit is sweet and sour, and is eaten as a fruit, juiced for drinking, or added to foodstuff or beverages such as jellies and cakes to add flavor. Passion fruit seeds are hard, and removed from the fruit when juiced. Even if the seeds are consumed with the fruit, the outer skin of the seeds is hard and difficult to digest, and the seeds are therefore excreted intact.

Conventionally, passion fruit seeds have been discarded without utilization; however, the applicants of the present invention reported that passion fruit seed extract can be effectively utilized as an active component for inhibiting melanin production or as an active component for enhancing collagen production (Patent Citations 1 and 2). The applicants also reported that the active component in question is piceatannol, which is a polyphenol compound (Patent Citation 3).

With regards to scirpusin B, which is a dimer of piceatannol, it has been reported that the substance has anti-HIV activity (Non-Patent Citation 1), has superoxide anion removal activity (Non-Patent Citation 2), has α-amylase activity inhibitory activity (Non-Patent Citation 3), and has xanthine oxidase inhibitory activity (Non-Patent Citation 4).

PATENT CITATIONS

[Patent Citation 1] Japanese Laid-Open Patent Application No. 2009-102298
[Patent Citation 2] Japanese Laid-Open Patent Application No. 2009-102299
[Patent Citation 3] Japanese Laid-Open Patent Application No. 2010-30911

NON-PATENT CITATIONS

[Non-Patent Citation 1] Guo-xun Yang, Jin-tao Zhou, Ya-zun Li, and Chang-qi Hu "Anti-HIV Bioactive stilbene dimers of *Caragana rosea*" Planta. Med. 71 (2005), p 569-571.
[Non-Patent Citation 2] Ting Xiang, Toshio Uno, Fumino Ogino, Cuoqian Ai, Jie Duo, and Ushio Sankawa "Antioxidant constituents of *Caragana tibetica*" Chem. Pharm. Bull. 53 (9) (2005), pp. 1204-1206.
[Non-Patent Citation 3] Kyoko Kobayashi, Tamaki Ishihara, Eriko Khono, Toshio Miyase, and Fumihiko Yoshizaki "Constituents of stem bark of *Callistemon rigidus* showing inhibitory effects on mouse α-amylase activity" Biol. Pharm. Bull, 29 (6), (2006) pp. 1275-1277.
[Non-Patent Citation 4] G. Schmeda-Hirschmann, M. I. Gutierrez, J. I. Loyola, and J. Zuniga "Biological activity and xanthine oxidase inhibitors from *Scirpus californicus* (C. A. Mey.) Steud" Phytotherapy Research, 10, (1996) pp. 683-685.

DISCLOSURE OF THE INVENTION

Problems to be Solved by the Invention

From a general viewpoint relating to food safety, scirpusin B added to foodstuff and beverages such as functional foods or health foods is preferably derived from a natural product. However, conventionally known natural products containing scirpusin B have a low scirpusin B content, and it has only been possible to obtain scirpusin-B-containing compositions having an extremely low scirpusin B content.

Accordingly, the object of the present invention is to provide a scirpusin-B-containing composition that is derived from a natural product and that contains a high level of scirpusin B, and to provide a method for manufacturing same.

Means to Solve the Problems

As a result of intensive research in order to achieve the above object, the inventors of the present invention discovered that passion fruit seeds, which have conventionally been discarded without utilization, contain a plentiful amount of scirpusin B, and arrived at the present invention.

Specifically, the scirpusin-B-containing composition according to the present invention is characterized in that the composition is obtained from passion fruit seeds and contains scirpusin B.

According to the scirpusin-B-containing composition of the present invention, it is possible to provide a composition that contains a high level of scirpusin B and that is derived from a natural product. Since the composition is derived from a natural product, the composition is suitable for being added to cosmetic products, pharmaceutical products, and foodstuff and beverages such as functional foods or health foods.

The method for manufacturing a scirpusin-B-containing composition according to the present invention, includes: adding at least one selected from a hydrous alcohol solvent and a hydrous ketone solvent to passion fruit seeds, and extracting scirpusin B into the solvent.

According to the method for manufacturing a scirpusin-B-containing composition of the present invention, since at least one selected from a hydrous alcohol solvent and a hydrous ketone solvent is added to passion fruit seeds, and scirpusin B is extracted into the solvent, a composition that is derived from a natural product and that contains a high level of scirpusin B can be manufactured at high yield.

In the method for manufacturing a scirpusin-B-containing composition according to the present invention, the passion fruit seeds are preferably raw passion fruit seeds or seeds obtained by drying raw passion fruit seeds.

In the method for manufacturing a scirpusin-B-containing composition, the hydrous alcohol solvent is preferably hydrous ethanol or hydrous 1,3-butylene glycol, or the hydrous ketone solvent is preferably hydrous acetone.

According to this arrangement, the efficiency of extracting scirpusin B is further improved.

In the method for manufacturing a scirpusin-B-containing composition according to the present invention, after the extraction, the solvent can be removed, or further condensed, spray-dried, freeze-dried, refined, or otherwise processed.

Another aspect of the present invention is a foodstuff or beverage having passion-fruit-seed-derived scirpusin B added thereto.

Another aspect of the present invention is a cosmetic having passion-fruit-seed-derived scirpusin B added thereto.

Advantageous Effects of the Invention

According to the scirpusin-B-containing composition of the present invention, it is possible to provide a composition that contains a high level of scirpusin B and that is derived from a natural product. Since the composition is derived from a natural product, the composition is suitable for being added to cosmetic products, pharmaceutical products, and foodstuff or beverages such as functional foods or health foods. According to the method for manufacturing a scirpusin-B-containing composition of the present invention, since at least one selected from a hydrous alcohol solvent and a hydrous ketone solvent is added to passion fruit seeds, and scirpusin B is extracted into the solvent, a composition that is derived from a natural product and that contains a high level of scirpusin B can be manufactured at high yield.

BEST MODE FOR CARRYING OUT THE INVENTION

Figure 1:
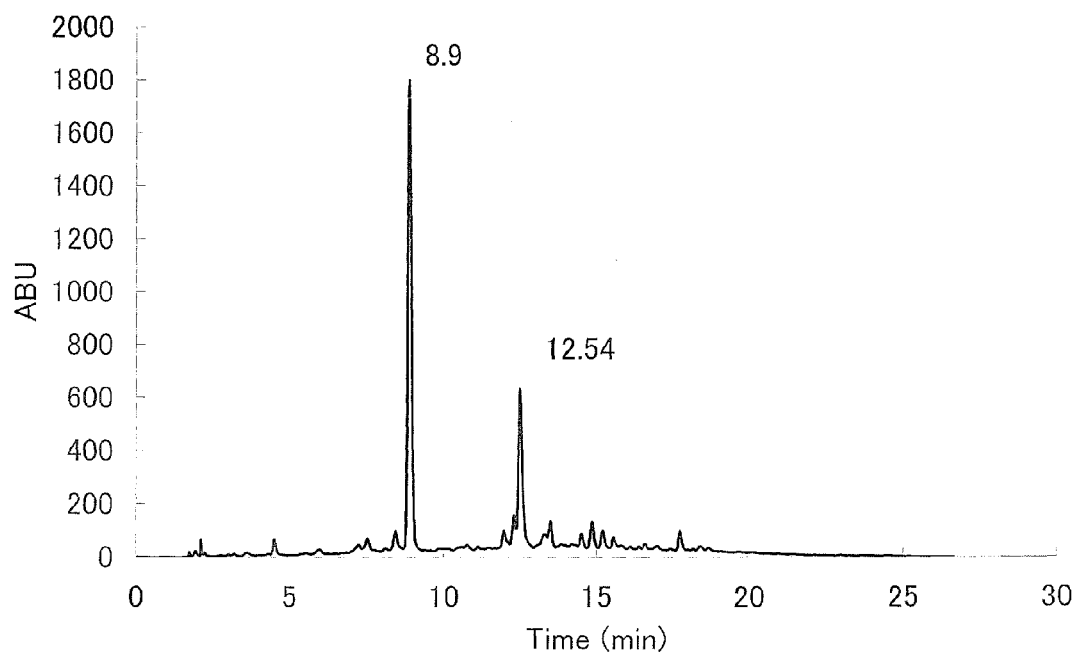
FIG. 1 shows a quantitative analytical HPLC chromatogram of scirpusin B from passion fruit seeds.

The scirpusin-B-containing composition of the present invention is obtained from passion fruit seeds and contains scirpusin B. The scirpusin-B-containing composition may be a liquid, a solid, a semi-solid, or a gel, and the amount of scirpusin B contained in the scirpusin-B-containing composition is preferably in the range of, e.g., $1\times10^{-6}$ mass % to 99.9 mass %, and further preferably in the range of, e.g., $1\times10^{-4}$ mass % to 20 mass %, and even further preferably in the range of, e.g., $1\times10^{-3}$ mass % to 5 mass %. The amount of scirpusin B contained in terms of solid content is preferably, e.g., 0.01 to 99.9 mass %, and further preferably, e.g., 0.05 to 30 mass %, and even further preferably, e.g., 0.1 to 20 mass %.

Scirpusin B is represented by the following chemical formula (1).

[Chemical formula 1]

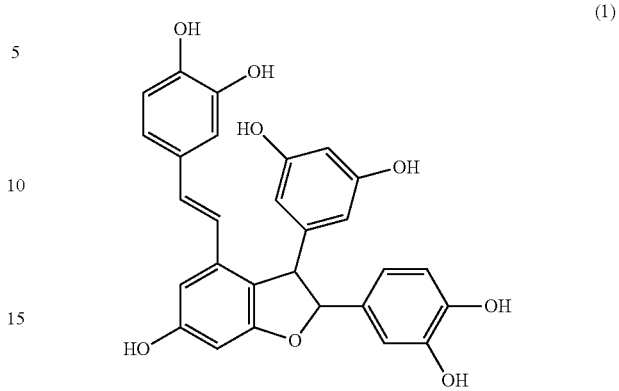

(1)

Passion fruit is a plant in the genus *Passiflora*, family Passifloraceae, known otherwise as *kudamono tokeiso*. The fruit is sweet and sour, and is eaten as a fruit, juiced for drinking, or added to foodstuff or beverages such as jellies and cakes to add flavor. Passion fruit seeds are hard, and removed from the fruit when juiced. Even if the seeds are consumed with the fruit, the outer skin of the seeds is hard and difficult to digest, and the seeds are therefore excreted intact. The present invention is based on the discovery that passion fruit seeds, which have conventionally been discarded without utilization, contain a plentiful amount of scirpusin B. Passion fruit seeds, which are used in the present invention, present no problems in terms of safety when added to foodstuff or beverages such as functional foods or health foods, as supported by conventional experiences of passion fruit consumption.

The scirpusin-B-containing composition according to the present invention is preferably obtained by a method in which, e.g., raw or dried passion fruit seeds are used directly or crushed, and extraction is performed using a variety of solvents. In order to improve extraction efficiency, the passion fruit seeds may be subjected to a chemical treatment such as acid or alkali decomposition or enzymatic decomposition before extraction. In addition, according to the method for manufacturing a scirpusin-B-containing composition of the present invention described further below, a composition containing a high level of scirpusin B can be obtained at a particularly high yield; therefore, the composition is most preferably obtained using the corresponding method.

The method for manufacturing a scirpusin-B-containing composition according to the present invention will now be described.

In the method for manufacturing a scirpusin-B-containing composition according to the present invention, raw or dried passion fruit seeds may be used. In order to improve extraction efficiency, the passion fruit seeds may be subjected to crushing, oil pressing, or a chemical treatment such as acid or alkali decomposition and enzymatic decomposition before extraction. The crushing may be performed using a conventionally known crusher. Passion fruit seeds contain a high level of oil, and may therefore become a paste after crushing.

Next, at least one selected from a hydrous alcohol solvent and a hydrous ketone solvent is added to the passion fruit seeds, and scirpusin B is extracted into the solvent. The extraction is preferably performed while being, e.g., stirred, shaken, or heated to reflux.

A hydrous solvent with solvent such as ethanol, methanol, propanol, and 1,3-butylene glycol can be used as the hydrous alcohol solvent; hydrous ethanol and hydrous 1,3-butylene glycol are preferred in particular. A hydrous solvent with solvent such as acetone, methyl ethyl ketone, diethyl ketone, and chloroacetone can be used as the hydrous ketone solvent; hydrous acetone is preferred in particular.

With regards to the water content, hydrous ethanol has an ethanol content of preferably 20 to 99.9% by volume, further preferably 40 to 99.9% by volume, and most preferably 60 to 80% by volume. Hydrous 1,3-butylene glycol has a 1,3-butylene glycol content of preferably 10 to 90% by volume, further preferably 20 to 60% by volume, and most preferably 30 to 50% by volume. Hydrous acetone has an acetone content of preferably 20 to 99.9% by volume, further preferably 40 to 99.9% by volume, and most preferably 60 to 80% by volume. It is undesirable for the water content to fall outside the ranges listed above because extracting scirpusin B will be less efficient. With regards to the expression of the water content of the hydrous solvent, e.g., 80 vol % ethanol, which contains 20% by volume of water, shall be expressed as "80% hydrous ethanol" for the sake of simplicity. Also, e.g., 70 vol % ethanol, which contains 30% by volume of water, shall be expressed as "70% hydrous ethanol." Also, e.g., 30 vol % 1,3-butylene glycol, which contains 70% by volume of water, shall be expressed as "70% hydrous BG." Also, e.g., 70 vol % acetone, which contains 30% by volume of water, shall be expressed as "70% hydrous acetone."

In the method for manufacturing a scirpusin-B-containing composition according to the present invention, the extraction may be performed using a known shaking device. It is preferable that the temperature is about 15 to 40° C. and the shaking time is about 0.5 to 3 hours. The extraction may be performed by shaking accompanied by ultrasonic vibration. According to this arrangement, passion fruit seeds which have been crushed and brought into contact with the solvent are subjected to vibration in an effective manner, making it possible to improve the efficiency of extracting scirpusin B into the solvent from the passion fruit seeds. The shaking accompanied by ultrasonic vibration may be applied by, e.g., a known ultrasound device.

In the method for manufacturing a scirpusin-B-containing composition according to the present invention, the extraction may be performed using a known method for heating to reflux using the hydrous alcohol solvent or the hydrous ketone solvent mentioned above. It is preferable that the heating temperature is about 60 to 95° C. and the reflux time is about 1 to 2 hours.

In the method for manufacturing a scirpusin-B-containing composition according to the present invention, the solvent may be distilled off under reduced pressure after the extraction. A composition that does not contain an organic solvent can thereby be obtained, and the composition can be made to conform to the relevant safety standards and the like as a food ingredient to be added to a foodstuff or beverage such as functional foods or health foods.

In the method for manufacturing a scirpusin-B-containing composition according to the present invention, extraction may be performed in stages using a plurality of solvents. It is thereby possible to manufacture a scirpusin-B-containing composition containing a high level of scirpusin B at a higher yield.

Specifically, e.g., passion fruit seeds are crushed. Then, either the hydrous alcohol solvent or the hydrous ketone solvent mentioned above is added; shaking, heating to reflux, or a similar process is performed; and scirpusin B is extracted into the solvent and a first extract is obtained. The resulting mixture is centrifugally or otherwise separated into the extract and a residue which has not been recovered as the extract. The other of the abovementioned solvents, which was not previously selected, is added to the residue; shaking, heating to reflux, or a similar process is performed; and scirpusin B is extracted into the solvent and a second extract is obtained. Then, the first extract and the second extract are mixed. It shall be apparent that the second extract can be utilized independently as a passion fruit seed extract.

Since it is possible that thus performing extraction in stages using a plurality of solvents, and subjecting the passion fruit seeds to the first extraction process using the hydrous alcohol solvent or the hydrous ketone solvent, cause the physical and other properties of the passion fruit seeds to change in a manner that is preferable for extraction, it is possible to expect the extraction efficiency during the subsequent second extraction process to be improved not only in an instance in which the abovementioned hydrous alcohol solvent or hydrous ketone solvent is used, but also in an instance in which another solvent is used.

The amount of scirpusin B contained in the extract of passion fruit seeds obtained using the above method is preferably in the range of, e.g., $1 \times 10^{-6}$ mass % to 99.9 mass %, and further preferably in the range of, e.g., $1 \times 10^{-4}$ mass % to 20 mass %, and even further preferably in the range of, e.g., $1 \times 10^{-3}$ mass % to 5 mass %. The amount of scirpusin B contained in terms of solid content is preferably, e.g., 0.01 to 99.9 mass %, and further preferably, e.g., 0.05 to 30 mass %, and even further preferably, e.g., 0.1 to 20 mass %. The scirpusin-B-containing composition may be a liquid obtained by using the extract directly or concentrating the extract. The scirpusin-B-containing composition may also be a powder obtained by freeze drying or spray drying. The scirpusin-B-containing composition is not limited to the above formats. Insoluble matter contained in the extract may be removed as appropriate by, e.g., filtration. The insoluble matter may be further crushed into fine particles.

The primary extract of passion fruit seeds obtained as above may be fractionated and refined, using scirpusin B as an indicator, by, e.g., ion exchange, size exclusion column chromatography, HPLC, gel filtration, or membrane separation, and the product may be used as the scirpusin-B-containing composition.

Figure 2:
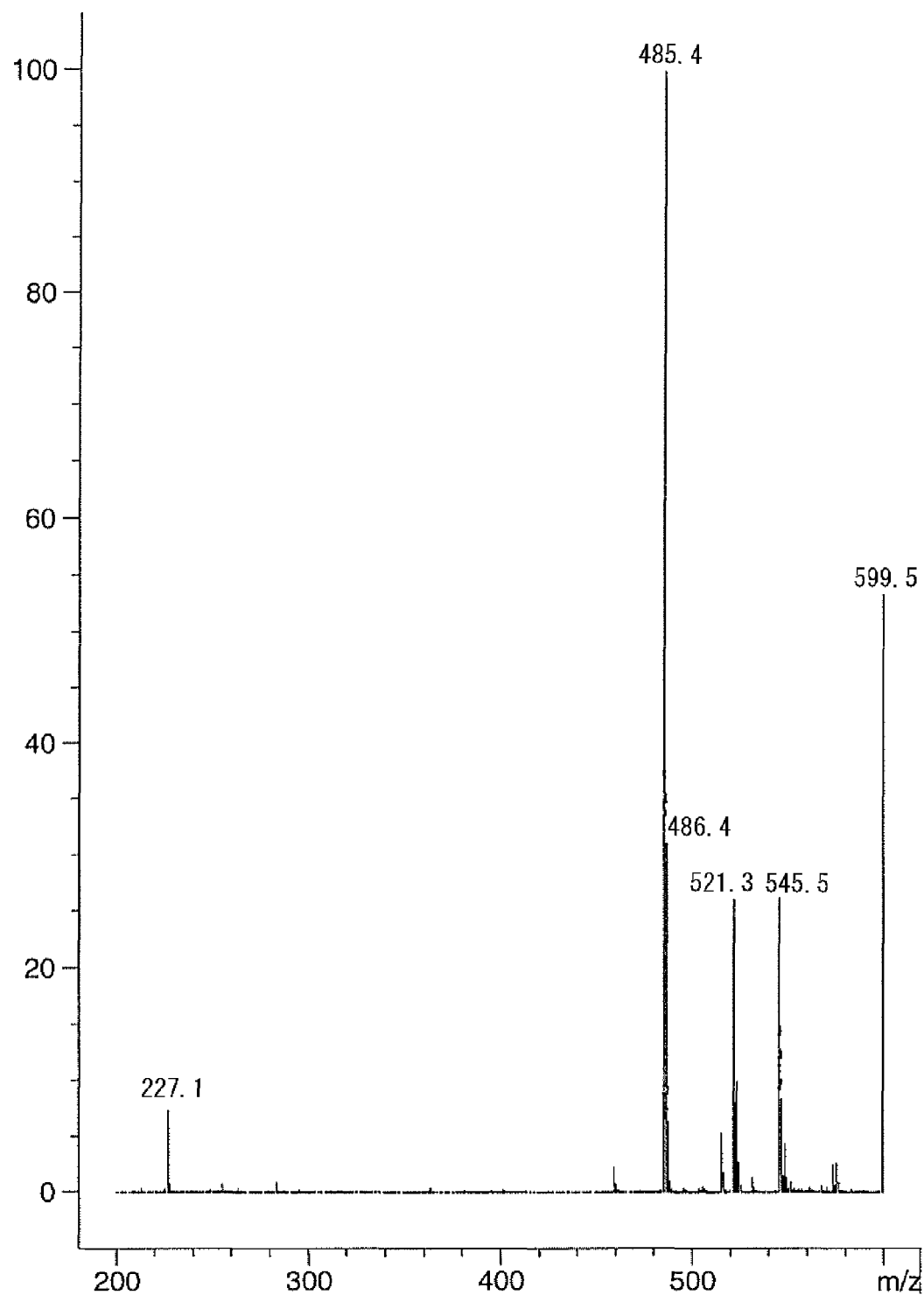
FIG. 2 shows a mass spectrum of scirpusin B from passion fruit seeds.

Specifically, when scirpusin B from passion fruit seeds is subjected to analytical HPLC under the following conditions, the scirpusin B is eluted in the vicinity of 12.54 minutes (see FIG. 1; the substance eluted in the vicinity of 8.9 minutes in FIG. 1 is piceatannol). Mass spectrometry performed using a mass spectrometer yields an m/z of 485 as a negative ion mode signal (see FIG. 2).

[HPLC Conditions]
  Column: ODS-3 diameter 4.6 mm, length 150 mm (GL Sciences)
  Column temperature: 45° C.
  Elution conditions: flow speed 0.75 ml/min, 15% acetonitrile (0 min)→40% acetonitrile (20 min)→45% acetonitrile (25 min)
  UV detection: 280 nm Therefore, in the present invention, it is possible to perform fractionation and refinement as appropriate while confirming the presence of scirpusin B from passion fruit seeds using the analysis means described above as an example and prepare a scirpusin-B-containing composition derived from passion fruit seeds having an increased scirpusin B content.

Scirpusin B derived from passion fruit seeds can have added thereto a pharmaceutically acceptable base material or carrier, made into tablets, granules, a powder, a liquid, a fine powder, fine granules, capsules, or jellies, etc. and used as a pharmaceutical product, or made into an ointment, a cream, a gel, a face mask, a lotion, or a cosmetic, etc. and used as a cosmetic product.

Scirpusin B derived from passion fruit seeds can also be added to foods for specified health uses, dietary supplements, or functional foods, etc. and consumed. Examples of such foods include: sweets such as chocolates, biscuits, chewing gums, candies, cookies, gummies, and tablet sweets; cereals; drinks such as drink powder, soft drinks, milk drinks, nutrition drinks, carbonated drinks, and jelly drinks; and cold sweets such as ice cream and sherbet. Other preferred examples include noodles such as soba, pasta, udon, and somen. The format for foods for specified health uses and dietary supplements may be a powder, granules, capsules, a syrup, tablets, and sugar-coated tablets.

In an instance in which scirpusin B derived from passion fruit seeds is added to a foodstuff or beverage or a cosmetic product and used, the amount of scirpusin B contained in the foodstuff or beverage or cosmetic product is preferably in the range of, e.g., $1 \times 10^{-6}$ mass % to 50 mass %, and further preferably in the range of, e.g., $1 \times 10^{-4}$ mass % to 20 mass %, and even further preferably in the range of, e.g., $1 \times 10^{-3}$ mass % to 5 mass %. The amount of scirpusin B contained in terms of solid content is preferably, e.g., 0.01 to 80 mass %, and further preferably, e.g., 0.05 to 30 mass %, and even further preferably, e.g., 0.1 to 20 mass %.

EXAMPLES

The present invention will now be described in a specific manner using examples; however, the examples are not intended to limit the scope of the present invention.

Test Example 1

Recovery, Refinement, and Identification of Scirpusin B from Passion Fruit 200 ml of 80% acetone is added to 60 g of crushed matter (30 to 60 mesh pass) obtained by freeze drying and crushing passion fruit seeds, and stirred at room temperature; and a seed extract liquid was produced. The liquid was fractionated by HPLC using an ODS column. The HPLC fractionation conditions were as follows.

Figure 3:
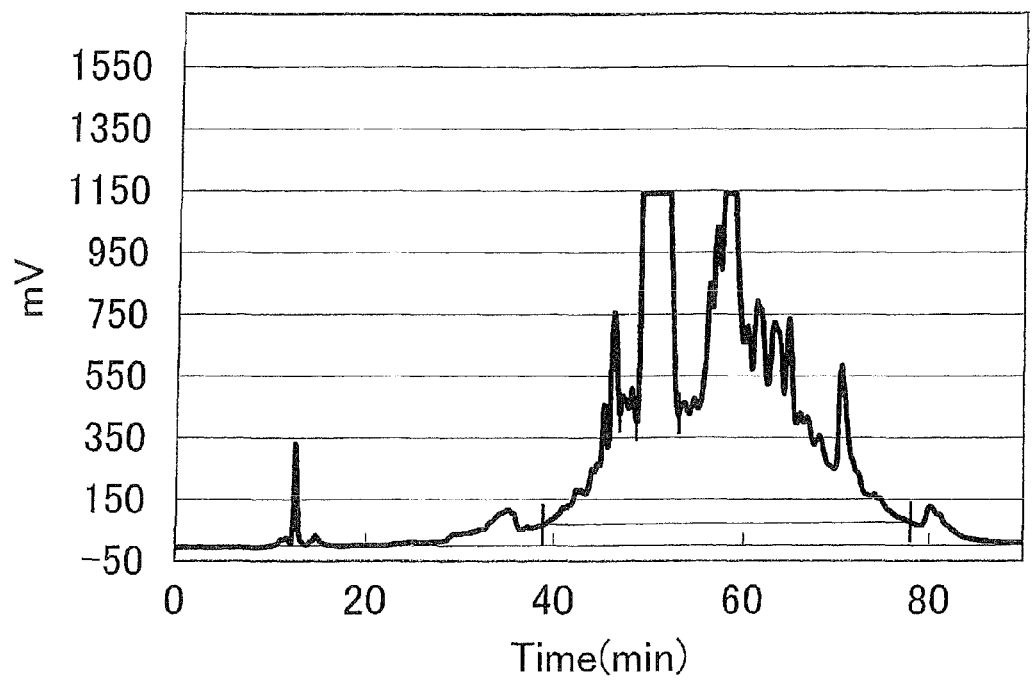
FIG. 3 is a HPLC chromatogram for fractionation of an extract from passion fruit seeds.

Column: ODS-3 diameter 20 mm, length 150 mm (GL Sciences)
Column temperature: room temperature
Elution conditions: flow speed 5 ml/min, 10% acetonitrile (0 min)→50% acetonitrile (70 min)→80% acetonitrile (75 min)→80% acetonitrile (90 min)
UV detection: 280 nm FIG. 3 shows the corresponding HPLC chromatogram. As a result, the largest peak was observed in the vicinity of a retention time of 51 minutes, and a second peak was observed in the vicinity of a retention time of 57 minutes.

The nature of the substance in the component eluted in the vicinity of a retention time of 57 minutes was identified as follows.

First, the fraction that is eluted in the vicinity of a retention time of 57 minutes was separated, and then refined to a purity of about 97% by further HPLC. The resultant was subjected to HPLC/mass spectrometry (Agilent 1100 LC/MC System; Agilent Technologies) and NMR analysis. The results are as follows.

ESI: m/z 485 (M−);
$^{1}$H NMR (CD30D, 500 MHz): δ4.38 (1H, d, J=6.0 Hz), δ5.32 ((1H, d, J=6.0 Hz), δ6.19 (2H, d, J=2.2 Hz), δ6.21 (1H, t, J=2.0 Hz), δ6.30 (1H, d, J=6.0 Hz), 6.58 (1H, d, J=16.1 Hz), 6.62 (1H, dd, J=2.2, 8.5 Hz) 6.66 (1H, d, J=1.9 Hz), δ6.68 (1H, d, J=7.8 Hz), 6.74 (1H, d, J=2.2 Hz) 6.78 (1H, d, J=8.2 Hz), 6.81 (1H, d, J=16.4 Hz), δ6.80 (1H, d, J=1.9 Hz);

$^{13}$C NMR: (CD30D, 125 MHz): δ: 58.1, 94.8, 96.8, 102.2, 104.4, 107.3x2, 113.6, 114.0, 116.2x2, 116.3, 118.4, 119.8, 120.0, 123.6, δ: 130.9, 131.0, 134.9, 137.0, 146.3, 146.4, 146.5, 146.6, 147.6, 159.8x3, 162.7

The above result of the NMR analysis showed that the substance is scirpusin B represented by formula (1) below.

[Chemical formula 2]

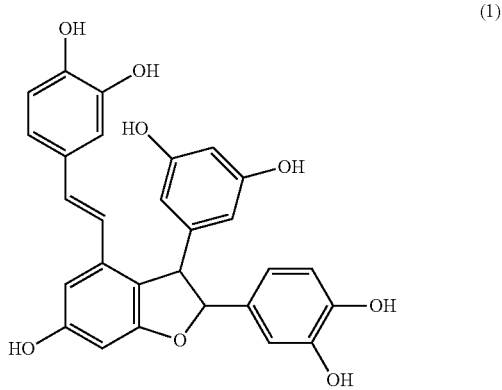

(1)

The optical rotation measurement (JASCO P-2200 polarimeter) of the component eluted in the vicinity of 57 minutes was $[\alpha]_D^{23}$:0.0°, and in the result of the infrared absorption spectrum obtained using a JASCO FT/IR-6200 Fourier-Transform Infrared Spectrometer, absorption peaks were present at 1605 cm$^{-1}$, 1520 cm$^{-1}$, 1445 cm$^{-1}$, 1339 cm$^{-1}$, 1282 cm$^{-1}$, 1197 cm$^{-1}$, 1156 cm$^{-1}$, 1116 cm$^{-1}$, and 1002 cm$^{-1}$. These results do not contradict the results of the above-mentioned identification. Results of analyzing the NMR, optical rotation, infrared absorption spectrum, etc. of scirpusin B are also set forth in Kyoko KOBAYASHI et al.; Biol. Pharm. Bull. 29(6), (2006) pp. 1275-1277.

The component eluted in the vicinity of a retention time of 51 minutes was separately identified to be piceatannol represented by formula (2) below.

[Chemical formula 3]

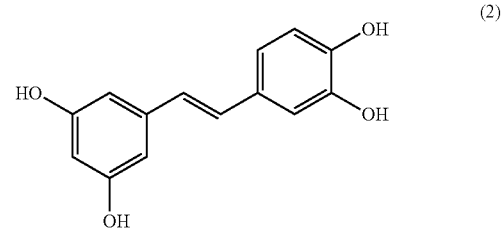

(2)

In light of the above, it was found that the peak in the vicinity of 57 minutes obtained by fractionation HPLC analysis of the seed extract corresponds to scirpusin B, and that passion fruit seeds contain a large amount of scirpusin B. No scirpusin B was detected in passion fruit peel or pulp.

Text Example 2

Extraction of Scirpusin B from Passion Fruit Seeds

It was examined on the extraction method of scirpusin B from the passion fruit seeds. More specifically, the extraction efficiencies of scirpusin B by the extraction methods described below were examined.

(1) Shaking Extraction Using Hydrous Ethanol and Hydrous Acetone 200 mL of 80% hydrous ethanol was added to 60 g of crushed seeds and shaken at room temperature for 30 minutes to perform extraction, and the resulting supernatant was recovered. This step was repeated twice. Then, 200 mL of 80% of hydrous acetone was added to the resulting solid residue and shaken at room temperature for 30 minutes to perform extraction, and the resulting supernatant was recovered. This step was repeated three times. Then, the extract liquid obtained by collecting the recovered supernatant was concentrated, brought to a constant volume of 200 ml using 80% hydrous ethanol, and 10 μl of the liquid was subjected to analytical HPLC. A calibration curve was created using a sample refined in advance to a high purity (97%), and the amount of scirpusin B contained in the extract was quantitatively determined.

(2) Extraction by Heating to Reflux Using Hydrous Ethanol 3 liters of 80%, 90%, or 95% hydrous ethanol was added to 300 g of crushed seeds, and extraction was performed by heating to reflux for 90 minutes at 92° C. Then, the extract liquid obtained was concentrated, brought to a constant volume of 200 ml using 80% hydrous ethanol, and 10 μl of the liquid was subjected to analytical HPLC. Then, the amount of scirpusin B contained in the extract liquid was quantitatively determined using a calibration curve created in advance.

(3) Extraction by Stirring Using 1,3-Butylene Glycol (Hydrous BG)

Approximately 100 ml of 20%, 40%, 50%, 60%, or 80% hydrous BG was added to 10 g of seeds that have been dried using hot air or further crushed, and extraction was performed by heating and stirring for 1 hour at 80° C. A portion of the extract liquid obtained was subjected to HPLC, and the amount of scirpusin B contained in the extract liquid was quantitatively determined using a calibration curve created in advance.

The results are shown in the following Tables 1 and 2. In Table 1, the results shown are converted into (A) the amount (mg) of scirpusin B extracted from 100 g of seeds used in the extraction, or (B) the scirpusin B content (mass %) in the solid content in the extract liquid.

TABLE 1

| | Scirpusin B | |
|---|---|---|
| | [A] Amount contained [mg] in 100 g of seeds | [B] Amount contained [mass %] in solid content of extract liquid |
| Shaking extraction | 283 | 2.5 |
| 80% EtOH reflux | 246 | 2.1 |
| 90% EtOH reflux | 363 | 3.2 |
| 95% EtOH reflux | 220 | 1.9 |

As shown in Table 1, 220 to 363 mg of scirpusin B per 100 g of passion fruit seeds was extracted. The amount contained in the solid content of the extract liquid according to each of the extraction methods was 2.5 mass % for shaking extraction, 2.1 mass % for extraction by heating to reflux using 80% hydrous ethanol, 3.2 mass % for extraction by heating to reflux using 90% hydrous ethanol; and 1.9 mass % for extraction by heating to reflux using 95% hydrous ethanol. Therefore, in the comparison of extraction methods, scirpusin B was most efficiently extracted by heating to reflux using 90% hydrous ethanol. When the scirpusin B content in passion fruit seeds was converted from the value corresponding to the most efficient extraction, it was found that passion fruit seeds contain scirpusin B in a large amount; i.e., at least about 0.36 mass %. It was also found that the scirpusin B can be efficiently extracted.

In Table 2, the results shown are converted into (A) the amount (mg) of scirpusin B extracted from 100 g of seeds used in the extraction, or (B) the scirpusin B content (μg/ml) in the extract liquid.

TABLE 2

| | Scirpusin B | |
|---|---|---|
| BG concentration | [A] Amount contained [mg] in 100 g of seeds | [B] Amount contained [μg/ml] in extract liquid |
| 20% hydrous BG | 185 | 223 |
| 40% hydrous BG | 401 | 485 |
| 50% hydrous BG | 92.6 | 61.7 |
| 60% hydrous BG | 313 | 378 |
| 80% hydrous BG | 260 | 314 |

* In the instance of 50% hydrous BG only, the seeds were not crushed.

As shown in Table 2, 92.6 to 401 mg of scirpusin B per 100 g of passion fruit seeds was extracted by extraction through stirring using hydrous 1,3-butylene glycol (hydrous BG). For the results shown for 50% hydrous BG, extraction was performed from whole seeds which have not been crushed. Although the extraction efficiency fell somewhat, it was confirmed that extraction is possible without crushing.

The invention claimed is:

1. A method for manufacturing a scirpusin-B-containing composition, comprising:
    adding an extraction solvent to passion fruit seeds,
    extracting scirpusin B into the solvent, and
    fractionating and/or refining the extracted scirpusin B to provide the scirpusin-B-containing composition with at least 0.1 mass % in terms of solid content of the scirpusin B.

2. The method for manufacturing a scirpusin-B-containing composition according to claim 1, wherein the passion fruit seeds are raw passion fruit seeds or seeds obtained by drying raw passion fruit seeds.

3. The method for manufacturing a scirpusin-B-containing composition according to claim 1, wherein the solvent is hydrous ethanol, hydrous 1,3-butylene glycol, or t hydrous acetone.

4. The method for manufacturing a scirpusin-B-containing composition according to claim 1, wherein the solvent is distilled off after the extraction.

5. The method for manufacturing a scirpusin-B-containing composition according to claim 1, wherein the fractionating and/or refining includes using scirpusin B as an indicator, by ion exchange, size exclusion column chromatography, HPLC, gel filtration, or membrane separation.

* * * * *